US00PP20940P2

(12) United States Plant Patent
Richards

(10) Patent No.: US PP20,940 P2
(45) Date of Patent: Apr. 20, 2010

(54) ***SALVIA* PLANT NAMED 'ICING SUGAR'**
(50) Latin Name: *Salvia greggii*
Varietal Denomination: Icing Sugar

(75) Inventor: Rodney William Richards, Mansell Gamage (GB)

(73) Assignee: New World Plants Ltd., Mansell Gamage, Herefordshire (GB)

( * ) Notice: Subject to any disclaimer, the term of this patent is extended or adjusted under 35 U.S.C. 154(b) by 0 days.

(21) Appl. No.: 12/291,553

(22) Filed: Nov. 12, 2008

(51) Int. Cl.
*A01H 5/00* (2006.01)

(52) U.S. Cl. ..... Plt./475
(58) Field of Classification Search ..... Plt./263, Plt./263.1, 475
See application file for complete search history.

*Primary Examiner*—Susan B McCormick Ewoldt
(74) *Attorney, Agent, or Firm*—C. A. Whealy

(57) ABSTRACT

A new and distinct cultivar of *Salvia* plant named 'Icing Sugar', characterized by its upright and relatively compact plant habit; strong growth habit; freely flowering habit; red purple and light purple bi-colored flowers; and good garden performance.

2 Drawing Sheets

Botanical designation: *Salvia greggii.*
Cultivar denomination: 'ICING SUGAR'.

BACKGROUND OF THE INVENTION

The present invention relates to a new and distinct cultivar of *Salvia* plant, botanically known as *Salvia greggii* and hereinafter referred to by the name 'Icing Sugar'.

The new *Salvia* plant originated from an open-pollination during the summer of 2004 of an unnamed selection of *Salvia greggii*, not patented, as the female, or seed, parent with an unknown selection of *Salvia greggii*, as the male, or pollen, parent. The new *Salvia* plant was discovered and selected by the Inventor as a single flowering plant from within the progeny of the stated open-pollination grown in a controlled outdoor nursery environment in Herefordshire, United Kingdom in 2005.

Asexual reproduction of the new cultivar by vegetative cuttings in Herefordshire, United Kingdom, since the spring of 2006, has shown that the unique features of this new *Salvia* plant are stable and reproduced true to type in successive generations.

SUMMARY OF THE INVENTION

Plants of the new *Salvia* have not been observed under all possible environmental conditions. The phenotype may vary somewhat with variations in environment such as temperature and light intensity without, however, any variance in genotype.

The following traits have been repeatedly observed and are determined to be the unique characteristics of 'Icing Sugar'. These characteristics in combination distinguish 'Icing Sugar' as a new and distinct cultivar:

1. Upright and relatively compact plant habit.
2. Strong growth habit.
3. Freely flowering habit.
4. Red purple and light purple bi-colored flowers.
5. Good garden performance.

Plants of the new *Salvia* can be compared to plants of the female parent selection. Plants of the new *Salvia* differ from plants of the female parent selection in the following characteristics:

1. Plants of the new *Salvia* are more compact than plants of the female parent selection.

2. Plants of the new *Salvia* have larger flowers than plants of the female parent selection.

Plants of the new *Salvia* can be compared to plants of 'Hot Lips', not patented. In side-by-side comparisons conducted in Herefordshire, United Kingdom, plants of the new *Salvia* differed from plants of 'Hot Lips' in the following characteristics:

1. Plants of the new *Salvia* had slightly larger flowers than plants of 'Hot Lips'.
2. Plants of the new *Salvia* and 'Hot Lips' differed in flower color as plants of 'Hot Lips' had red and white bi-colored flowers.
3. Plants of the new *Salvia* and 'Hot Lips' differed in sepal color as plants of 'Hot Lips' had yellow green-colored sepals.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia.*

The photograph on the first sheet comprises a side perspective view of typical flowering plants of 'Icing Sugar' grown in an outdoor nursery.

The photograph on the second sheet is a close-up view of typical flowers and leaves of 'Icing Sugar'.

DETAILED BOTANICAL DESCRIPTION

Plants used for the aforementioned photographs and following description were grown under conditions which closely approximate commercial production conditions during the late spring through the summer in an outdoor nursery in Boijl, The Netherlands. During the production of the plants, day temperatures ranged from 15° C. to 30° C. and night temperatures ranged from 10° C. to 15° C. Plants had been growing for six months when the photographs and description were taken. In the following description, color references are made to The Royal Horticultural Society Colour Chart, 2001 Edition, except where general terms of ordinary dictionary significance are used.

Botanical classification: *Salvia greggii* 'Icing Sugar'.

Parentage:

*Female, or seed, parent*.—Unnamed selection of *Salvia greggii*, not patented.

*Male, or pollen, parent*.—Unknown selection of *Salvia greggii*, not patented.

Propagation:

*Type*.—By cuttings.

*Time to initiate roots*.—About 15 days at 20° C.

*Time to produce a rooted young plant*.—About 20 to 28 days at 20° C.

*Root description*.—Fine, fibrous; white in color.

*Rooting habit*.—Freely branching; moderately dense.

Plant description:

*Type*.—Herbaceous perennial.

*Form*.—Upright and relatively compact plant form; strong growth habit. Flowers arranged in upright verticillasters on spikes.

*Branching habit*.—Freely basal branching with about ten main stems.

*Growth habit*.—Vigorous.

*Plant height*.—About 45 cm.

*Plant width*.—About 10 cm to 15 cm.

*Lateral branch description*.—Length: About 8 cm to 10 cm. Diameter: About 3 mm. Internode length: About 4.5 cm. Strength: Strong. Aspect: Mostly upright. Texture: Pubescent. Color: Close to 144A.

Foliage description:

*Arrangement*.—Opposite, simple.

*Length*.—About 2 cm to 3 cm.

*Width*.—About 1.5 cm to 2 cm.

*Shape*.—Ovate.

*Apex*.—Acute.

*Base*.—Attenuate.

*Margin*.—Serrate to crenate.

*Texture, upper and lower surfaces*.—Rough, glabrous; waxy.

*Venation pattern*.—Pinnate.

*Color*.—Developing and fully expanded leaves, upper surface: Close to 137B; venation, close to 144C. Developing and fully expanded leaves, lower surface: Close to 137C; venation, close to 144B.

*Petiole length*.—About 5 mm.

*Petiole diameter*.—About 5 mm.

*Petiole texture, upper and lower surfaces*.—Smooth, glabrous.

*Petiole color, upper and lower surfaces*.—Close to 137B.

Flower description:

*Flower arrangement and shape*.—Single bilabiate flowers arranged in verticillasters in whorls with eight to twelve per spike; flowers face mostly outwardly. Freely flowering habit, about 50 to 70 flowers per plant.

*Fragrance*.—Faint.

*Natural flowering season*.—Continuous flowering from spring to late autumn in The Netherlands.

*Flower longevity on the plant*.—About two weeks; flowers not persistent.

*Flower buds*.—Length: About 1 cm to 1.5 cm. Diameter: About 3 mm. Shape: Oblong. Color: Close to 71A.

*Inflorescence size*.—Length: About 8 cm to 10 cm. Diameter: About 5 cm.

*Flowers*.—Length: About 2 cm to 3 mm. Diameter: About 1.5 cm. Depth (height): About 3 cm.

*Petals*.—Arrangement: Two lips, fused at the base. Length, upper lip: About 9 mm. Length, lower lip: About 1.2 cm. Width, upper lip: About 3 mm. Width, lower lip: About 1.5 cm. Shape, upper lip: Broadly elliptic; apex, acute; base, attenuate; margin, entire. Shape, lower lip: Roughly orbicular; apex, two-lobed and broad; base, attenuate; margin, entire. Texture, upper and lower surfaces: Smooth, glabrous; satiny. Color, upper lip: When opening, upper and lower surfaces: Close to N74B. Fully opened, upper surface: Close to N74B. Fully opened, lower surface: Close to 68A. Color, lower lip: When opening, upper surface: Close to 76C. When opening, lower surface: Close to 68A. Fully opened, upper surface: Close to N74B; towards the margins, close to 76C; margins becoming closer to 73A with development. Fully opened, lower surface: Close to 76C.

*Sepals*.—Arrangement: Two; opposite; fused at base. Length: About 1 cm. Width: About 3 mm to 4 mm. Shape: Deltoid. Apex: Acute. Margin: Entire. Texture, upper and lower surfaces: Smooth, glabrous. Color, upper and lower surfaces: Close to 144B overlain with close to 187A.

*Pedicels*.—Strength: Moderately strong. Length: About 5 mm. Diameter: About 1 mm. Aspect: About 40° from vertical. Texture: Smooth, glabrous. Color: Close to 184D.

*Reproductive organs*.—Stamens: Quantity per flower: Two. Filament length: About 5 mm. Filament color: Close to 155A. Anther shape: Ovate. Anther length: About 8 mm. Anther color: Close to 16B. Pollen amount: Moderate. Pollen color: Close to 15C. Pistils: Quantity per flower: One. Pistil length: About 2.7 cm. Stigma shape: Two-parted. Stigma color: Close to 67A. Style length: About 2.5 cm. Style color: Close to 155C. Ovary color: Close to 5C.

*Seed/fruit*.—Seed and fruit production has not been observed.

Disease/pest resistance: Plants of the new *Salvia* have not been noted to be resistant to pathogens and pests common to *Salvia*.

Garden performance: Plants of the new *Salvia* have exhibited good garden performance and to be tolerant to rain, wind and temperatures ranging from about −5° C. to about 35° C.

It is claimed:

1. A new and distinct *Salvia* plant named 'Icing Sugar' as illustrated and described.

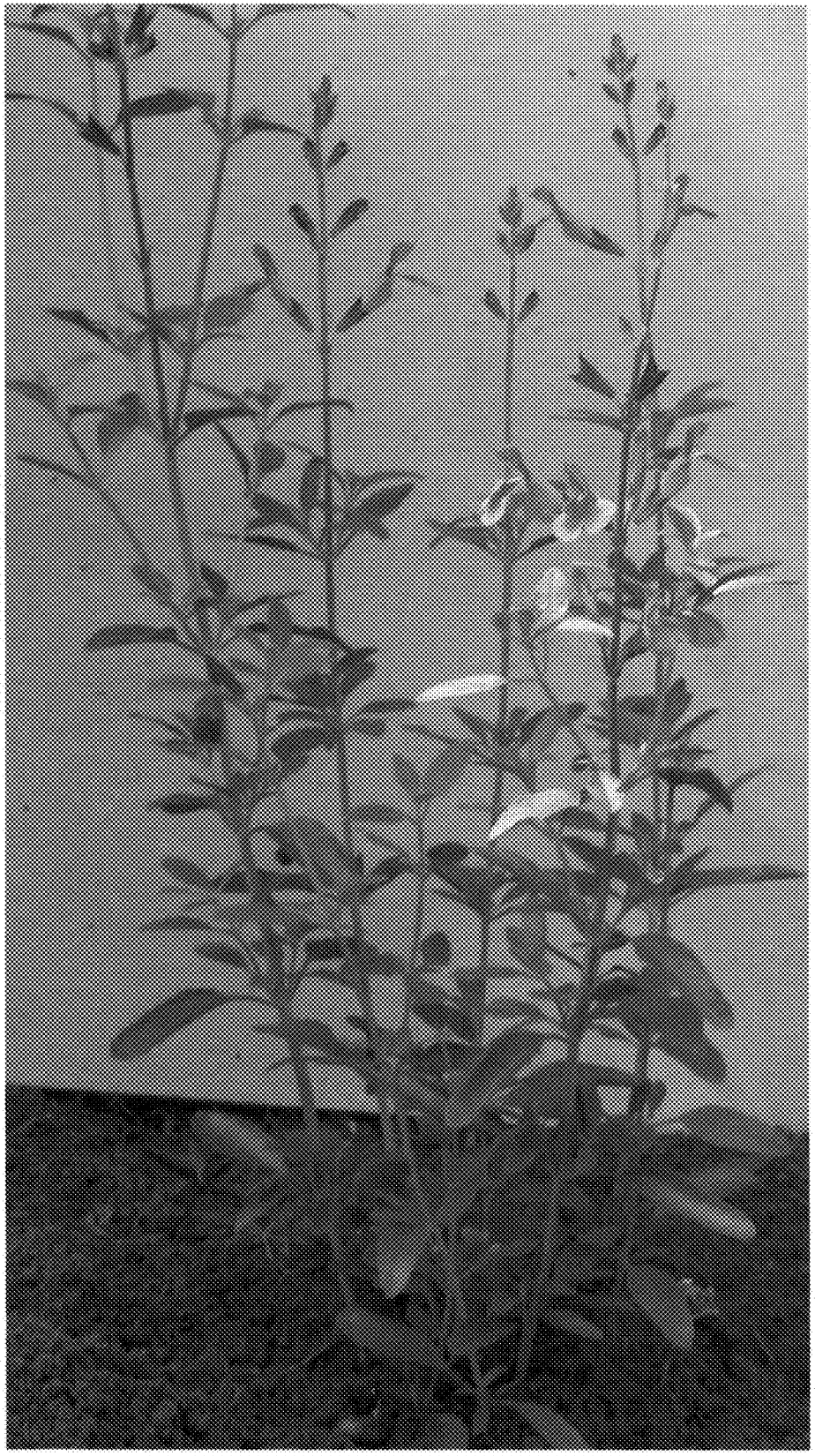

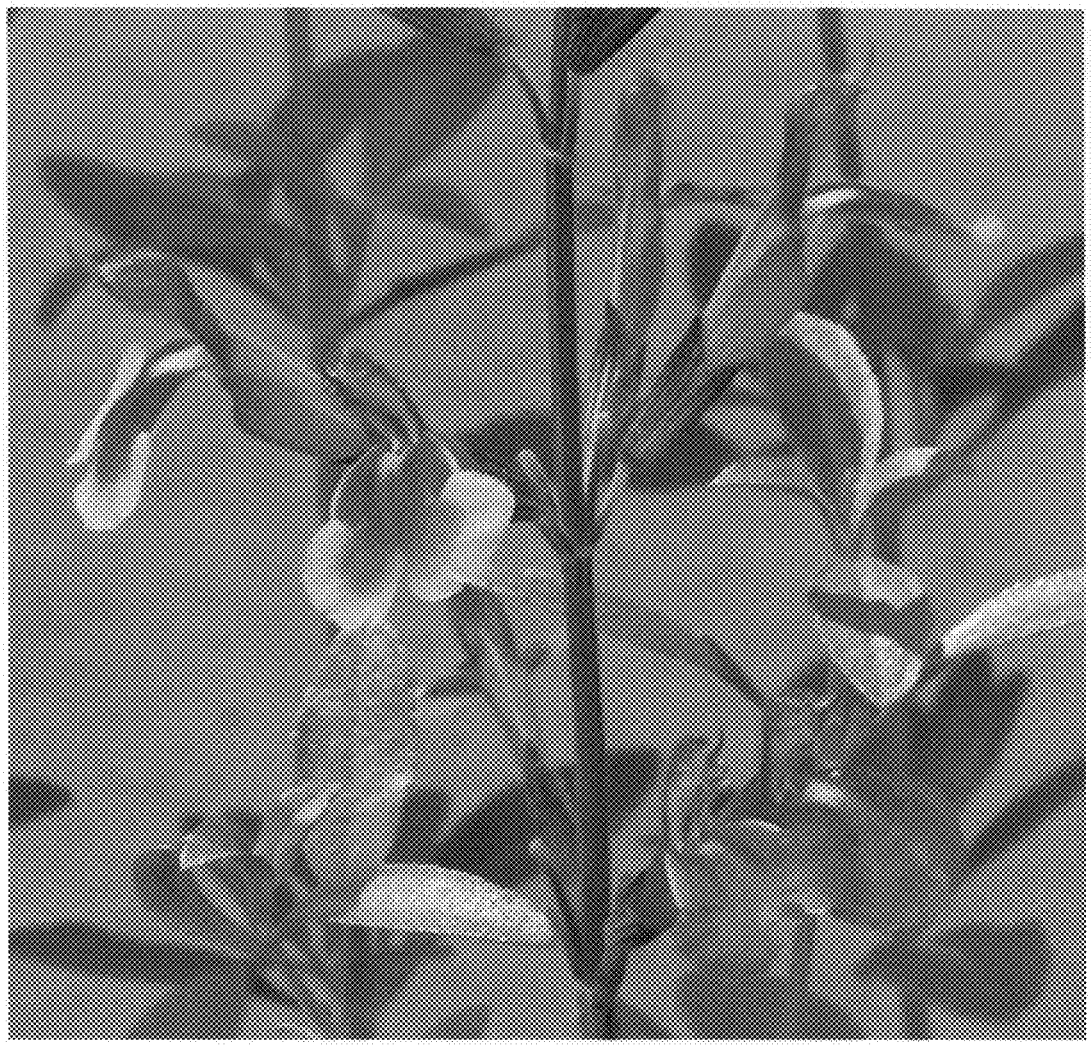

* * * * *